(12) United States Patent
Philipp et al.

(10) Patent No.: US 10,349,839 B2
(45) Date of Patent: Jul. 16, 2019

(54) IMPLANTABLE PRESSURE SENSOR DEVICE

(71) Applicant: BIOTRONIK SE & Co. KG, Berlin (DE)

(72) Inventors: Jens Philipp, Berlin (DE); Joachim Elsner, Berlin (DE); Sarah Biela, Berlin (DE); Alois Pfenniger, Biel (CH); Andreas Bitzer, Zurich (CH); Henning Ebert, Berlin (DE); Olaf Skerl, Bad Doberan (DE); Andre van Ooyen, Berlin (DE)

(73) Assignee: BIOTRONIK SE & CO. (DE)

( * ) Notice: Subject to any disclaimer, the term of this patent is extended or adjusted under 35 U.S.C. 154(b) by 514 days.

(21) Appl. No.: 15/045,693

(22) Filed: Feb. 17, 2016

(65) Prior Publication Data

US 2016/0249818 A1    Sep. 1, 2016

(30) Foreign Application Priority Data

Feb. 27, 2015 (DE) .................. 10 2015 102 863
Feb. 27, 2015 (EP) .................... 15156953

(51) Int. Cl.
*A61B 5/02* (2006.01)
*A61B 5/0215* (2006.01)
(Continued)

(52) U.S. Cl.
CPC ........ *A61B 5/0215* (2013.01); *A61B 5/02141* (2013.01); *A61B 5/686* (2013.01); *A61B 2562/0247* (2013.01)

(58) Field of Classification Search
CPC ... A61B 5/0215; A61B 5/021; A61B 5/02141; A61B 5/686; B81B 2201/0264; B81B 2203/0127; G01L 19/04
See application file for complete search history.

(56) References Cited

U.S. PATENT DOCUMENTS 3,046,788 A * 7/1962 Laimins ................ G01L 9/0002
                                                        338/4
4,407,296 A   10/1983 Anderson
(Continued)

FOREIGN PATENT DOCUMENTS

DE          24 20 610 A1    10/1975
DE     10 2011 054732 A1     4/2013
(Continued)

OTHER PUBLICATIONS

European Search Report, 15156953.0-1657, dated Aug. 21, 2015.
German Search Report, dated Oct. 9, 2015.

*Primary Examiner* — Eric J Messersmith
(74) *Attorney, Agent, or Firm* — Craig A. Fieschko, Esq.; DeWitt LLP

(57) ABSTRACT

An implantable pressure sensor device (100) has a housing (10) which is at least partially made of a pressure transmitting membrane (20), and which includes one or more regions which can reversibly deform while maintaining the surface area of the membrane (20) when the internal volume of the housing (10) is changed. The housing (10) has a non-circular cross-section which can deform to a more circular shape when pressure in the internal volume increases. An inner housing is preferably situated within the housing, with its exterior spaced from the interior of the housing, and has its inner volume in fluid communication with the space between the housing and inner housing.

22 Claims, 2 Drawing Sheets

(51) Int. Cl.
*A61B 5/021* (2006.01)
*A61B 5/00* (2006.01)

(56) References Cited

U.S. PATENT DOCUMENTS

| | | | |
|---|---|---|---|
| 6,638,231 | B2 | 10/2003 | Govari et al. |
| 8,142,362 | B2 | 3/2012 | Keilman et al. |
| 8,209,031 | B1 | 6/2012 | Rodriguez et al. |
| 8,573,062 | B2 | 11/2013 | Zhao et al. |
| 9,541,462 | B2 * | 1/2017 | Adams .................... G01P 15/08 |
| 2002/0077553 | A1 | 6/2002 | Govari et al. |
| 2005/0268722 | A1 * | 12/2005 | Tai ........................... A61B 3/16 |
| | | | 73/715 |
| 2009/0270740 | A1 * | 10/2009 | Keilman .............. A61B 5/0215 |
| | | | 600/486 |
| 2014/0005569 | A1 | 1/2014 | Miethke |

FOREIGN PATENT DOCUMENTS

| | | |
|---|---|---|
| EP | 1 216 653 A1 | 6/2002 |
| WO | WO 2012/052078 A1 | 4/2012 |

* cited by examiner

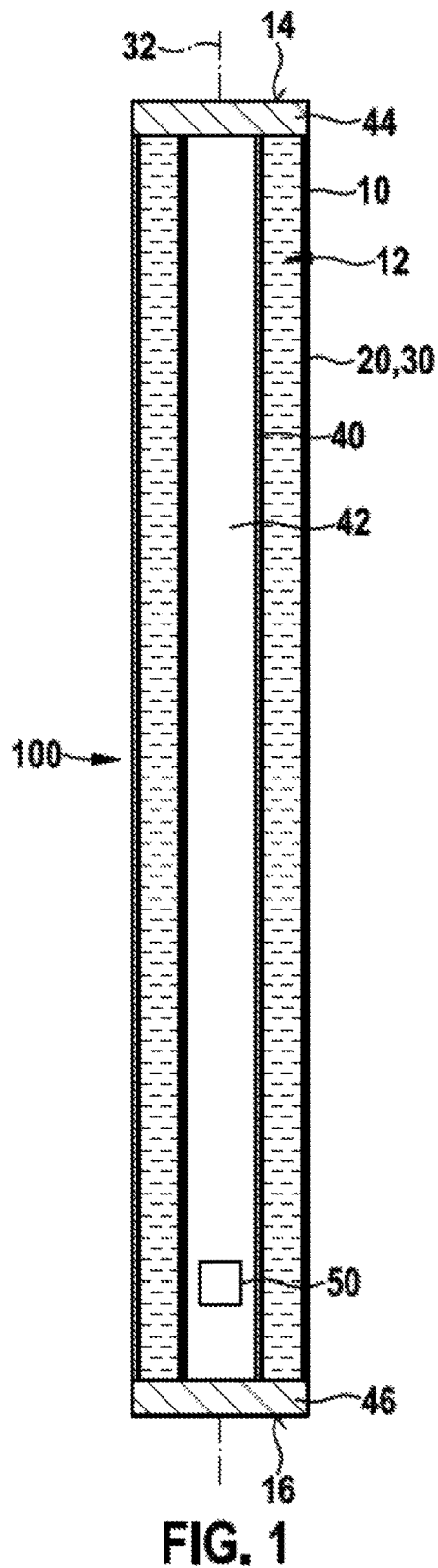
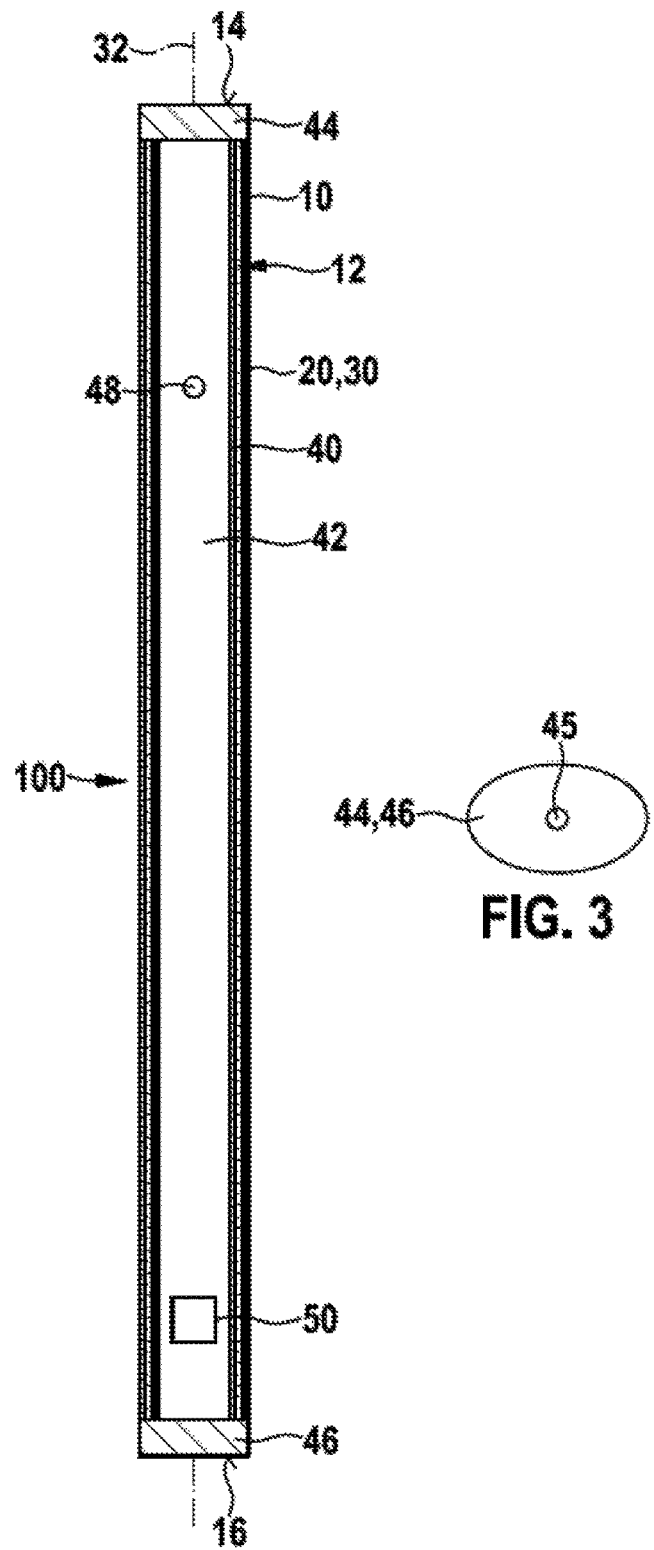
FIG. 1  FIG. 2  FIG. 3

IMPLANTABLE PRESSURE SENSOR DEVICE

FIELD OF THE INVENTION

The invention relates to an implantable pressure sensor device, in particular to a miniature pressure sensor device which is implantable in an animal or human body.

BACKGROUND OF THE INVENTION

Pressure sensor devices which include microelectromechanical system (MEMS) chips are used as implants, for example, as an implantable cardiac device which may be implanted in a patient to improve the function of the patient's heart. Such MEMS chips can have dimensions of less than 1 mm by 1 mm by 0.3 mm, and can deliver precise pressure measurements with an accuracy of 2 mbar or less.

For usage in a reactive medium such as blood, MEMS chips are usually embedded in an inert liquid and hermetically sealed against the reactive medium for protection of the chips. Typical constructions use metallic housings having a window covered with a pressure transmitting membrane. For medical implants, titanium is usually chosen because of its biocompatibility and long-time stability. The MEMS chip is arranged in an incompressible and inert liquid, such as oil, inside the housing. A typical thickness of the housing is more than 100 µm and the window with the pressure transmitting membrane is arranged at a front face of the housing (see U.S. Pat. No. 8,142,362), or in the wall of the housing (see U.S. Pat. No. 8,573,062).

SUMMARY OF EXEMPLARY VERSIONS OF THE INVENTION

The invention seeks to provide an implantable pressure sensor device which is predominantly insensitive to temperature changes in its operating environment. The implantable pressure sensor device includes a housing with an interior volume, wherein the housing is at least partially made of a pressure transmitting membrane having a surface area. The housing includes one or more regions which are reversibly deformable while maintaining the size of the membrane's surface area when the housing's interior volume is changed. A microelectromechanical pressure sensor chip is preferably situated within the interior volume enclosed within the housing, or is otherwise coupled to the interior volume.

Preferably, at least 5% of the housing is made of the pressure transmitting membrane, though the entire housing can be made of the pressure transmitting membrane. The membrane has increased flexibility so that the pressure measurement resolution is improved, in particular, by decreasing the pressure load on the membrane generated by thermally-initiated volume increases of the liquid inside the housing. The housing of the implantable pressure sensor device preferably has a volume of less than 100 mm$^3$, and more preferably less than 60 mm$^3$. Similarly, the housing of the implantable pressure sensor device preferably has a diameter of less than 10 mm, and more preferably less than 6 mm.

The interior volume includes an incompressible liquid, such as oil, as a medium for transmitting pressure from outside the housing to the inside of the housing, and to the pressure sensor located therein. The flexible membrane compensates for changes of the volume of the incompressible liquid in the housing caused by temperature variations during manufacture and operation without creating high pressure levels in the liquid. High pressure levels can cause nonreversible or nonlinear deformations of the membrane, and/or can damage the embedded sensor, leading to errors in the pressure reading. By providing the housing (or at least a significant portion of the housing) as a membrane instead of providing a membrane defined as a window in the housing, the surface of the membrane can be significantly increased. As a result, the membrane is better able to compensate for volume expansion of the incompressible liquid, and pressure increase inside the housing. Despite miniaturization of the pressure sensor device below a diameter of 5 mm, the device may have a temperature coefficient $\Delta P/\Delta T$ of 10 mbar/K or less (this coefficient defining the pressure increase inside the incompressible liquid as a function of its temperature).

A convenient membrane material is titanium, which has good biocompatibility and long-term stability, and may be formed as a membrane and sealed in a hermetically tight manner. However, the elastic modulus of titanium is high, which creates a challenging problem when a membrane is required for housing diameters of less than 5 mm (as is desired for cardiac and other implants). In particular, where an external pressure is to be transferred across a membrane to an internal volume, the membrane will resist the external load and dampen the transfer of the pressure from the membrane's exterior to its interior.

In a preferred version of the inventive sensor, the membrane may include one or more regions which allow for reversible deformation while maintaining the size of the membrane's surface area when the interior volume of the housing is changed. The membrane defines at least a portion of the housing. By minimizing tensile stress in the membrane material, the effect of pressure increases inside the housing can be reduced. The geometry of the housing may be irregular, in particular encompassing housing geometries which are non-circular or otherwise lack rotational symmetry, as by having an elliptical, triangular, or rectangular housing cross-section. When the fluid volume inside the housing increases, the housing's cross-section changes to a "rounder" one which nearly (or fully) has rotational symmetry. In contrast to normal stress applied to a longitudinal axis of the membrane, which results in normal strain and material expansion, the deformation described above is dominated by bending effects where the load is applied perpendicular to a longitudinal axis of the membrane, and regions of tensile stress are compensated by regions of compressive stress. As a result, the overall tensile stress in the membrane vanishes as well as longitudinal expansion of the membrane material.

As an example, the housing's geometry and/or topology may be configured to provide a temperature coefficient $\Delta P/\Delta T$ of not more than 10 mbar/K, and more preferably of not more than 5 mbar/K, which is more than two orders of magnitude below the conventional arrangement wherein the membrane is provided as a window in the housing.

Due to the low temperature coefficient of the housing, various tolerances have lower effect on the pressure sensing capabilities of the inventive sensor. For instance, manufacturing tolerances which may increase the oil volume have only an insignificant effect on the temperature coefficient. The functional dependency of the pressure versus volume change exhibits linear behavior over a significantly larger range than that of a typical front face mounted membrane window, which tends to have a rather cubic dependency $(\Delta V_{oil}(\Delta T))^3$. Because the ratio of membrane area to the membrane rim area is much larger for the inventive sensor, tolerances which reduce the active membrane area, e.g. weld seams, interfere to a lesser extent. Plastic deformations in the housing occurring during manufacturing—such as dents, kinks and the like—may in some cases be favorable for the temperature coefficient, as these defects are additional irregular regions which allow for reversible deformation when the housing's internal volume changes.

The inventive pressure sensor device is also tolerant to high volume increases during thermal sterilization procedures. Typical temperatures for sterilization procedures are 55° C. or more, at least 20 K higher than standard body temperature. Von Mises tensions inside the membrane material remain in an elastic range such that the housing is not plastically deformed during sterilization, avoiding the necessity of recalibrating the pressure sensor after sterilization.

Tolerances resulting from air bubbles introduced when filling the housing with pressure transmitting liquid do not dampen the pressure transmission, as the membrane can compensate for the effect of air bubbles.

The housing may be configured as a tube with an elliptical cross section which deforms towards a circular cross section when the volume inside the housing increases. The tube may predominantly or completely consist of the membrane. Because the elliptical cross section may change to a circular cross section when the internal volume is increased, the strain on the membrane remains low.

The sensor chip may be surrounded by the pressure transmitting membrane, thereby maximizing the surface area of the membrane for a given overall size of the sensor device.

In a conventional sensor membrane arrangement wherein a sensor housing bears a window covered by a membrane at a front face of the housing, in accordance with plate/membrane theory from continuum mechanics (which only takes into account mechanical tensile stress inside the membrane), the pressure $\Delta P_{membrane}$ of a conventional titanium membrane behaves according to the relation $\Delta P_{membrane} \sim (\Delta V_{oil}(\Delta T))^3 \cdot h \cdot E/F^5$, wherein h is membrane thickness, E is elastic modulus, and F is the membrane area. The temperature coefficient $\Delta P/\Delta T$ for this arrangement is large, and the temperature induced pressure measurement error becomes so large that it cannot be compensated by prediction/simulation of temperature effects. The large temperature coefficient $\Delta P/\Delta T$ is primarily a result of the tensile stress in the membrane induced by the volume increase inside the housing.

Typical miniaturized pressure sensor devices have liquid volume of about 25 mm$^3$, which requires large membrane diameters of more than 5 mm if $\Delta P/\Delta T$ is not to exceed 10 mbar/K.

For a sensor housing consisting of a tube with an elliptical cross section, in accordance with plate/membrane theory from continuum mechanics (which only takes into account forces perpendicular to the plate/membrane), the pressure change $\Delta P_{membrane}$ of the membrane behaves according to the relation $\Delta P_{membrane} \sim (\Delta V_{oil}(\Delta T))^3 \cdot h^3 \cdot E/F^3$, wherein h is membrane thickness, E is elastic modulus, and F is the membrane area. The temperature coefficient $\Delta P/\Delta T$ for this arrangement is much smaller than in the conventional sensor membrane arrangement, by up to two orders of magnitude, so that a temperature coefficient $\Delta P/\Delta T$ of below 10 mbar/K can be reliably achieved even for sensor housing diameters below 5 mm diameter.

The front face of the sensor housing may be provided with an opening for introducing a liquid (e.g., oil) into the housing. The liquid can be introduced into the housing, which can be easily sealed afterwards. The opening can also or alternatively provide a passage for an electrical connection from the pressure sensor chip within the housing with the outside of the housing.

The thickness of the membrane is preferably not more than 30 μm, and more preferably not more than 25 μm. This provides sufficient flexibility while also providing stability for the sensor housing.

The membrane may include a corrugated inner surface, which may provide the membrane with anisotropic flexural properties. As an example, where the housing is a tube, the corrugated inner surface of the membrane may include valleys and ridges oriented parallel to the longitudinal axis of the tube. The membrane is then more pliant and receptive to flexure parallel to the valleys and ridges, and more stiff and resistant to flexure perpendicular to the valleys and ridges. The stability of the housing and membrane can be improved, making the pressure sensor device less sensitive to handling and transport.

An inner housing may be situated within the housing, wherein the inner housing encloses the pressure sensor chip. An interior volume of the inner housing is then in fluid connection to the outside of the inner housing. Within the inner housing, the pressure sensor chip may be more securely situated within the housing and protected against mechanical damage. The inner housing may be provided as a tube having elliptical plates situated at its opposing front faces, with the membrane connected to the elliptical plates. The inner housing may also include one or more channels, where a guide wire may thread in and through the housing.

The use of a deformable housing to compensate for volume changes can be useful in other areas too, for instance to compensate for volume changes caused by chemical processes in Li-ion batteries.

BRIEF DESCRIPTION OF THE DRAWINGS

The accompanying drawings show exemplary versions of the invention described in the following Detailed Description section of this document, with the drawings depicting:

FIG. 1: a cross-sectional view of an exemplary pressure sensor device having an elliptical cross section, as seen from the major axis;

FIG. 2: a cross-sectional view of the pressure sensor device of FIG. 1 seen from the minor axis;

FIG. 3: a top view of an elliptical front plate of the pressure sensor device of FIG. 1;

Figure 4:
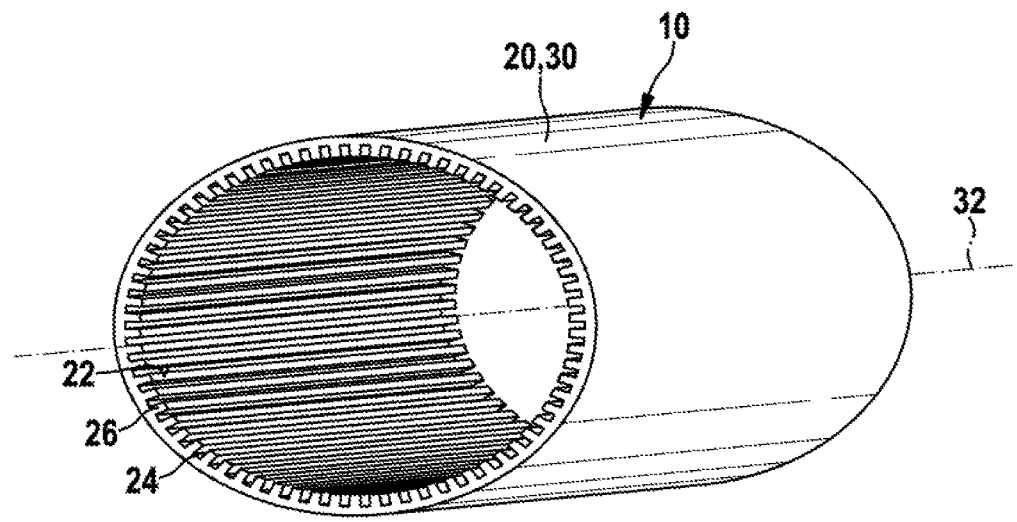
FIG. 4: a perspective view of a portion of a membrane tube having a corrugated inner surface.

In the drawings, like elements are referred to with the same reference numerals. The drawings are merely schematic representations, and are not intended to portray specific parameters of the invention. Moreover, the drawings depict only exemplary versions of the invention, and the invention is not limited to these exemplary versions.

The dimensions and values given in the following Detailed Description are exemplary, and may be different in other versions of the invention.

DETAILED DESCRIPTION OF EXEMPLARY VERSIONS OF THE INVENTION

FIGS. 1 to 3 schematically depict an exemplary version of the invention in a cross-sectional view and a top view. A pressure sensor device 100 includes a housing 10 enclosing an inner volume 12 filled with an incompressible liquid such as oil. The pressure sensor device 100 is configured as a miniaturized device suitable for implantation into a human or animal body. A typical volume of such a miniaturized pressure sensor device 100 may be in the range of about 50 mm³.

The housing 10 includes a tube 30 closed by two opposing front faces 14/16. An inner housing 40 is situated within the housing 10, with the inner housing 40 enclosing a MEMS pressure sensor chip schematically depicted at 50. Components such as electric cabling, electronic equipment and the like, which are well known to a person skilled in the art, may be arranged in the inner housing 40, but are not shown.

The tube 30 of the housing 10 includes a membrane 20, preferably made of titanium and having a thickness of not more than 30 μm, more preferably not more than 25 μm.

The inner housing 40 is a tube with (for example) a diameter of 1.2 mm, a length of 20 mm, and a wall thickness of 100 μm. The inner housing includes an opening 48 to establish a fluid connection between the MEMS pressure sensor chip 50 and the membrane 20.

The housing 10, and thus the membrane 20, have an elliptical cross section as can be seen by comparison of FIGS. 1 and 2. Such an irregular shape of the membrane 20 reduces tensile stress on the membrane 20 when the volume of the liquid increases with increasing temperature. The membrane 20 can compensate for the volume increase $\Delta V_{oil}(\Delta T)$ by deforming to a regular shape, i.e., by changing from an elliptic cross section to a circular cross section. A cylinder with circular cross section has a larger area, and thus a larger volume.

Elliptic plates 44/46, preferably made of titanium, are welded or otherwise connected to the front faces 14/16 of the inner housing 40. The minor axes of the plates 44/46 are larger than the diameter of the inner housing 40. Exemplary dimensions for the plates 44/46 are 1.3 mm along the major axis, 0.7 mm along the minor axis, and 0.5 mm thickness.

As seen in FIG. 3, an opening 45 in one of the plates 44/46 provides an inlet for filling the inner volume 12 with liquid. In one possible arrangement, the plates 44/46 at the front faces 14/16 provide one or more openings 45 for electrical cables, wherein the openings 45 serve as feedthrough openings for supplying the electric components of the pressure sensor device 100 with power.

The membrane 20 is welded or otherwise connected to the plates 44/46 attached to the inner housing 40. Exemplary dimensions for the membrane 20 are an area of about 120 mm², a major axis of 1.3 mm, a minor axis of 0.7 mm, a length of 20 mm, and 10 μm thickness.

With the exemplary dimensions above, the oil volume in the housing 10 is about 50 mm³, and 10 mm³ for the inner housing 40. A temperature difference of 10 K results in a volume change of $\Delta V_{oil}(10\ K) \sim 0.5$ mm³. This number is much lower than in a conventional arrangement with a membrane situated in a window on a front face of a housing.

Typical temperature variation in an animal or human body is $\Delta T \sim 1$ K, which leads to an approximate temperature dependent volume change $\Delta V_{oil}(\Delta T)$, where oil is used as the liquid, of $\Delta V_{oil}(\Delta T) = \gamma_{oil} \cdot V_{oil} \sim 0.001 \cdot V_{oil}$, with $\gamma_{oil}$ being the expansion coefficient of oil between 25° C. and 100° C. Assuming temperature measurements (taken concurrently with the pressure measurements for the purpose of correcting the pressure calculations) are about 0.1 K, it is useful to have a temperature coefficient $\Delta P/\Delta T$ for the membrane of not more than 10 mbar/K in order to determine the pressure with an accuracy of about 2 mbar. The membrane therefore has to be flexible enough that the resulting pressure increase generated by the volume change $\Delta V_{oil}$ is less than 10 mbar.

In a conventional arrangement with a membrane situated in a window on a front face of a housing, in accordance with plate/membrane theory from continuum mechanics (which only takes into account mechanical tensile stress), the pressure $\Delta P_{membrane}$ of a conventional titanium membrane behaves according to the relation $\Delta P_{membrane} \sim (\Delta V_{oil}(\Delta T))^3 \cdot h \cdot E/F^5$, wherein h is membrane thickness, E is elastic modulus, and F is the membrane area. The temperature coefficient $\Delta P/\Delta T$ for this arrangement is large, and the temperature-induced pressure measurement error becomes so large that it cannot be compensated by deduction of temperature-related effects. A predominant factor for the large temperature coefficient $\Delta P/\Delta T$ is the tensile stress in the membrane induced by the internal pressure increase inside the housing.

For a housing defined by a tube with an elliptical cross section, plate/membrane theory from continuum mechanics shows that the pressure change $\Delta P_{membrane}$ of the membrane behaves according to the relation $\Delta P_{membrane} \sim (\Delta V_{oil}(\Delta T))^3 \cdot h^3 \cdot E/F^3$, wherein h is membrane thickness, E is elastic modulus, and F is the membrane area. The temperature coefficient $\Delta P/\Delta T$ for this arrangement is much smaller than in the conventional arrangement, by up to two orders of magnitude, so that a temperature coefficient $\Delta P/\Delta T$ of well below 10 mbar/K can be reliably achieved even for housing diameters below 5 mm.

FIG. 4 illustrates an exemplary membrane 20 formed as a tube 30 having a corrugated inner surface 22 with valleys 24 and ridges 26 parallel to a longitudinal axis 32 of the tube 30. As exemplary dimensions, the membrane thickness at the ridges 26 may be 25 μm and the thickness at the valleys 24 may be 10 μm. Use of thicker membranes can provide greater resistance to external effects during transport and implantation.

Figure 5:
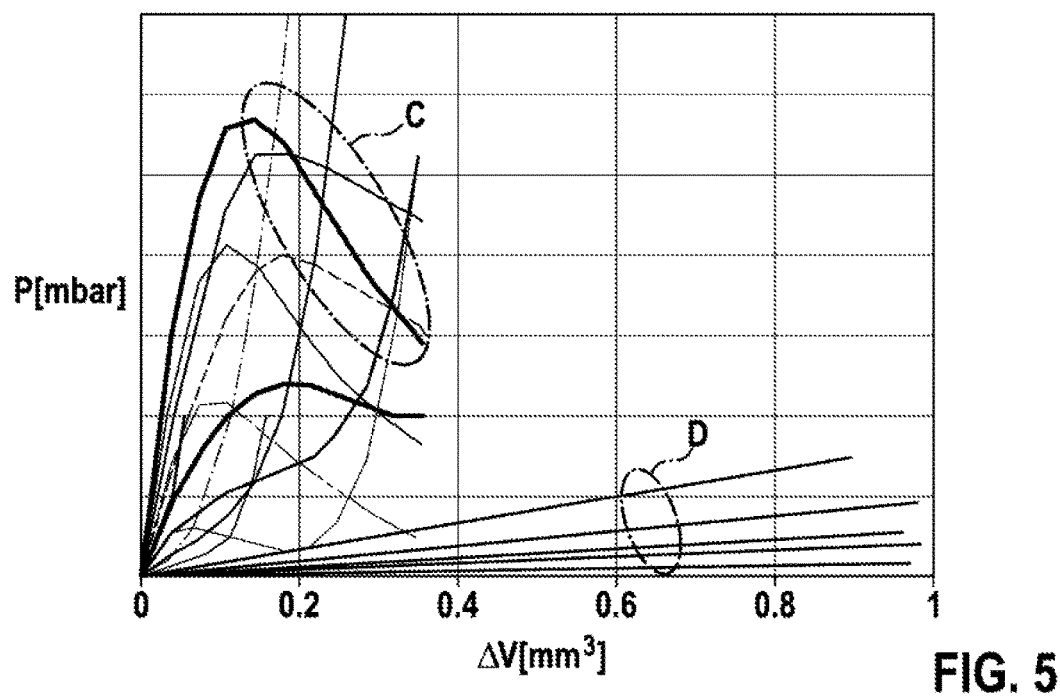
FIG. 5: a chart depicting the pressure-volume relationships of membrane tubes with various cross sections compared to known front face mounted membranes.

FIG. 5 illustrates calculated pressure-volume relationships of membrane tubes with various cross-sections compared to conventional front face-mounted membranes. A family of curves generally referred to as C represents the behavior of conventional front face-mounted membranes, exhibiting a very steep dependency of the pressure P depending on a thermally induced volume increase $\Delta V$. The family of curves generally denoted by D represents the behavior of tubular membranes as described herein having circular, elliptical, square, triangular and other cross-sections. The curves show a nearly linear behavior of the pressure P depending on the volume increase $\Delta V$ and show only a minor dependency on the cross-sectional shape.

What is claimed is:
1. An implantable pressure sensor device (100) including a housing (10) having an interior volume (12), wherein:
   a. the housing is at least partially formed of a pressure transmitting membrane (20) having a surface area,
   b. the housing includes one or more regions which are reversibly deformable while maintaining the size of the membrane's (20) surface area when the interior volume (12) is changed,
   c. the interior volume (2) includes:
      (1) an incompressible liquid, and
      (2) a pressure sensor (50),
   therein.
2. The device of claim 1 wherein at least 5% of the housing (10) is formed of the pressure transmitting membrane (20).

3. The device of claim 1 wherein the membrane (20) is configured to generate a temperature coefficient ΔP/ΔT of not more than 10 mbar/K.

4. The device of claim 1 wherein a thickness of the membrane (20) is not more than 30 μm, preferably not more than 25 μm.

5. The device of claim 1 wherein the pressure sensor (50) is surrounded by the pressure transmitting membrane (20).

6. The device of claim 1 further
including an inner housing (40) within the housing (10), the inner housing (40) surrounding the pressure sensor (50).

7. The device of claim 6 wherein an interior volume (42) of the inner housing (40) is in fluid connection with a volume defined between the housing (10) and the inner housing (40).

8. The device of claim 7 wherein the inner housing (40) is a tube (30) extending between opposing elliptical plates (44/46).

9. The device of claim 8 wherein the membrane (20) is connected between the elliptical plates (44/46).

10. The device of claim 1 wherein the housing (10) is configured as a tube (30) with an elliptical cross section.

11. The device of claim 1 wherein:
a. the housing (10) is configured as a tube (30) extending between opposing front faces (14/16),
b. at least one of the front faces (14/16) has an opening (18) configured to introduce a liquid into the housing (10).

12. The device of claim 1 wherein the membrane (20) has a corrugated inner surface (22).

13. The device of claim 12 wherein the housing (10) is configured as a tube (30) having a longitudinal axis (32).

14. The device of claim 9 wherein the corrugated inner surface (22) of the membrane (20) includes valleys (24) and ridges (26) extending parallel to the longitudinal axis (32).

15. The device of claim 1:
a. wherein the tube (30) of the housing (10) extends between opposing front faces (14/16);
b. further including an inner housing (40):
(1) configured as a tube (30) spaced inwardly from the housing (10),
(2) having an interior volume (42) in fluid connection with the space between the housing (10) and the inner housing (40).

16. An implantable pressure sensor device (100) including a housing (10) having an interior volume (12), wherein the housing:
a. is at least partially formed of a pressure transmitting membrane (20) having a surface area,
b. includes one or more regions which are reversibly deformable while maintaining the size of the membrane's (20) surface area when the interior volume (12) is changed,
c. is configured as a tube (30):
(1) extending between opposing front faces (14/16), the front faces (14/16) having non-circular perimeters from which the tube (30) extends;
(2) having a cross-section which is:
(a) less circular when the membrane (20) is not deformed, and
(b) more circular when the membrane (20) is deformed by pressure higher in the interior volume (12) of the housing (10) than outside the housing (10).

17. The device of claim 16 further including an inner housing (40) within the housing (10), the inner housing (40) being configured as a tube (30):
a. spaced inwardly from the housing (10), and
b. extending between the front faces (14/16),
wherein an interior volume (42) of the inner housing (40) is in fluid connection with the space defined between the housing (10) and the inner housing (40).

18. The device of claim 17 further including a pressure sensor (50) within the inner housing (40).

19. The device of claim 15 wherein:
a. the front faces (14/16) have noncircular perimeters from which the tube (30) extends, and
b. the cross-sectional shape of the tube (30) adopts the shape of the noncircular perimeters when the membrane (20) is not deformed.

20. An implantable pressure sensor device (100) including
a. a housing (10) having:
(1) a tube (30) extending between opposing front faces (14/16),
(2) an interior volume (12) within the tube (30) and the front faces (14/16), the housing being at least partially formed of a pressure transmitting membrane (20) configured to:
i. reversibly deform, and
ii. maintain its surface area,
when the interior volume (12) of the housing (10) changes;
b. an inner housing (40):
(1) configured as a tube (30) situated within, and spaced inwardly from, the housing (10),
(2) having an interior volume (42) in fluid connection with the space between the housing (10) and the inner housing (40).

21. The implantable pressure sensor device (100) of claim 20 wherein the membrane (20) has a corrugated inner surface.

22. The implantable pressure sensor device (100) of claim 16 wherein the membrane (20) has a corrugated inner surface.

* * * * *